(12) United States Patent  (10) Patent No.: US 7,068,491 B1
Burdon et al.  (45) Date of Patent: Jun. 27, 2006

(54) IMPLANTABLE CO-FIRED ELECTRICAL INTERCONNECT SYSTEMS AND DEVICES AND METHODS OF FABRICATION THEREFOR

(75) Inventors: Jeremy W. Burdon, Minneapolis, MN (US); Shawn D. Knowles, St. Francis, MN (US); Joyce K. Yamamoto, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/227,341

(22) Filed: Sep. 15, 2005

(51) Int. Cl.
*H01G 4/16* (2006.01)

(52) U.S. Cl. .................... 361/313; 361/321.2; 607/5

(58) Field of Classification Search ........ 361/311–313, 361/321.2, 321.3, 306.3; 607/4–5, 1
See application file for complete search history.

(56) References Cited

U.S. PATENT DOCUMENTS

| | | | |
|---|---|---|---|
| 5,032,692 A | * | 7/1991 | DeVolder .................. 174/52.3 |
| 5,999,398 A | * | 12/1999 | Makl et al. .................. 361/302 |
| 6,349,025 B1 | * | 2/2002 | Fraley et al. ............... 361/302 |
| 6,687,118 B1 | * | 2/2004 | O'Phelan et al. ........... 361/508 |

* cited by examiner

*Primary Examiner*—Anthony Dinkins
(74) *Attorney, Agent, or Firm*—Paul H. McDowall; Girma Wolde-Michael

(57) ABSTRACT

The invention includes a family of miniaturized, hermetic electrical feedthrough assemblies having at least one passive electrical component electrically coupled to a conductive pathway traversing each said assembly which are adapted for implantation within a biological system. The electrical feedthrough assembly according to the invention can be used as a component of an implantable medical device (IMD) such as an implantable pulse generator, cardioverter-defibrillator, physiologic sensor, drug-delivery system and the like. Such assemblies require biocompatibility and resistance to degradation under applied bias current or voltage. Such an assembly is fabricated by interconnected electrical pathways, or vias, of a conductive metallic paste disposed between ceramic green-state material. The layers are stacked together and sintered to form a substantially monolithic dielectric structure with at least one embedded metallization pathway extending through the structure.

20 Claims, 3 Drawing Sheets

IMPLANTABLE CO-FIRED ELECTRICAL INTERCONNECT SYSTEMS AND DEVICES AND METHODS OF FABRICATION THEREFOR

CROSS REFERENCE TO RELATED APPLICATIONS

This patent disclosure is related to U.S. patent application Ser. No. 11/227,375 entitled, "MINIATURIZED CO-FIRED ELECTRICAL INTERCONNECTS FOR IMPLANTABLE MEDICAL DEVICES," U.S. patent application Ser. No. 11/227,523 entitled, "MULTI-PATH, MONO-POLAR CO-FIRED HERMETIC ELECTRICAL FEEDTHROUGHS AND METHODS OF FABRICATION THEREFOR," and U.S. patent application Ser. No. 11/227,342 entitled, "IMPLANTABLE CO-FIRED ELECTRICAL FEEDTHROUGHS," each of which were filed on even date hereof and each of which is hereby incorporated by reference herein.

FIELD

The invention relates to selectively conductive hermetic electrical feedthrough structures having at least one passive electrical component electrically adapted coupled to a conductive pathway traversing each the structure; and, in particular such structures adapted for implantation within a biological system.

BACKGROUND

Miniaturized electrical feedthroughs are required for implantable medical devices (IMDs) that offer reduced functional volume in a small package while offering a high level of electromagnetic interference (EMI) protection. In conventional feedthrough technologies, EMI filtering is oftentimes accomplished by mounting chip-type capacitors or discoidal capacitors on the surface of an electrical feedthrough. This technology suffers from the disadvantage of increasing overall device volume while increasing lead interconnect length required to attach the termination of the capacitor to the hermetic pin assembly and grounding structure (typically the ferrule and a portion of the outer enclosure of a metallic IMD). Technologies are required that enable integration of EMI protection while improving the electrical performance in a very small, low-profile, miniaturized device structure.

To the inventors' present knowledge, the prior-art does not disclose or render obvious the invention set forth herein.

SUMMARY

Unlike some prior art methods and apparatus, certain embodiments of the present invention involve use of low temperature co-fired ceramic (LTCC), high temperature co-fired ceramic (HTCC) and combinations of both LTCC and HTCC fabrication and processing methods and structures. In general, such ceramic structures are formed using particles of high temperature-withstanding dielectric material such as alumina and glass suspended in an organic binder and formed and dried into so-called green sheets. Individual sheets (or segments of tape) are printed with a metallized paste and other circuit patterns, stacked on each other, laminated together and subjected to a predetermined temperature and pressure regimen, and then fired at an elevated temperature(s) during which the majority of binder material(s) (present in the ceramic) and solvent(s) (present in the metallized paste) vaporizes and/or is incinerated while the remaining material fuses or sinters. Where alumina glass is generally used as the insulating material, platinum, iridium, platinum-iridium alloys, tungsten, molybdenum and/or molymanganese or other suitable materials are typically constitute the metallized paste. Thus, the green sheets are patterned and then stacked and aligned in an appropriate laminated configuration. The stacked laminates are then fired at temperatures of about 600 to about 800 degrees Celsius (for LTCC) and about 1300 to about 1600 degrees Celsius (for HTCC) in a reducing atmosphere such as hydrogen. Both LTCC and HTCC technology typically employs high-melting point refractory metal pastes as conductors.

The invention includes a family of miniaturized, hermetic electrical feedthrough assemblies having at least one passive electrical component electrically coupled to a conductive pathway traversing each said assembly which are adapted for implantation within a biological system. The electrical feedthrough assembly according to the invention can be used as a component of an implantable medical device (IMD) such as an implantable pulse generator, cardioverter-defibrillator, physiologic sensor, drug-delivery system and the like. Such assemblies require biocompatibility and resistance to degradation under applied bias current or voltage. Such an assembly is fabricated by interconnected electrical pathways, or vias, of a conductive metallic paste disposed between ceramic green-state material. The layers are stacked together and sintered to form a substantially monolithic dielectric structure with at least one embedded metallization pathway extending through the structure.

Co-fire technology is an enabling technology for reduced FT size and increase density, and presents unique integration options for EMI filtering technology and associated interconnects. The technology allows device size to be greatly reduced, while increasing the device density and functionality, and offers a low-cost route to part fabrication. Conventional feedthrough technologies deploy components (for example, ceramic insulator and Niobium pin) that are assembled and processed to form the functional device. In co-fire technology, the insulator and metallization for electrical interconnect are processed together in a pre-sintered stage and then fired to form a monolithic feedthrough structure. This has a number of advantages over conventional feedthrough technologies, including providing 3D integration architectures for embedding components and electrical interconnects, thereby providing increased performance while allowing device miniaturization.

Integration of capacitors in a co-fireable feedthrough structure offers a number of significant advantages over current feedthrough technologies both in terms of final device size and electrical performance. This applies to use of both surface-mounted-technologies (SMT's) and fully integrated components. In co-fire technology, an SMT device such as a capacitor can be integrated by mounting in a cavity formed during the multilayer fabrication of the co-fire structure. The effective current loop of the capacitor will be reduced thereby lowering the parasitic inductance and the interconnect length will be reduced. Multilayer architectures enabled by co-fire technology allow interconnects to be buried within the feedthrough structure. This offers the ability to reduce overall lead-interconnect length to integrated components, reducing interconnect path length to individual electrical feedthroughs and critical grounding structures such as ground signal vias, or to external ferrule interconnect structures. This reduced lead-interconnect length contributes to the lowering of the parasitic inductance thereby improving EMI-filtering performance.

In as much as co-fire technology is the preferred embodiment to realize the disclosed invention, alternative 3D integration platform technologies such as high-density interconnect (HDI) and multilayer printed wiring board (PWB) are also enabling technologies for component integration and may be used in conjunction with a ed hermetic electrical feedthrough to provide increased performance in a more compact device.

As illustrated in FIG. 1, prior art SMT capacitors are available in a variety of sizes (wherein an SMT capacitor having dimensions such as 0.020"×0.010" is coded as 0201). Other common sizes include a 0.40"×0.020" which is coded as 0402 (others of course can be used, such as 0603, 0805, etc). SMT capacitors are typically square or rectangular shaped with end-terminations designed for surface mounting. For IMDs requiring filtering of low-voltage signals from sensing devices an exemplary embodiment involves use of reduced-size capacitor technologies offered by devices coded as 0402 and 0201 (in dimension). For high-voltage applications, SMT capacitors coded as within the 0603 and 0805 size range or below provide advantages and serves as another exemplary embodiment. Device integration is not limited to capacitors adapted for EMI filtering; other discrete devices capable of integration into co-fire feedthrough structures include bypass capacitors, resistors and inductors.

Numerous capacitor integration connection schemes exist that may be deployed to form permanent, electrically viable, high performance interconnects. In a typical application for implantable devices such as in implantable pulse generators (IPGs) and implantable cardiac defibrillators (ICDs), passive components such as EMI filtering capacitors are oftentimes mounted on the interior of the device. As many metallized areas and dielectric surfaces of an IMD are not exposed to bodily fluids, a variety of standard materials and processes can be used for providing electrical interconnections between components and circuits of the IMD. Termination metallizations for capacitors are well known in the art and include, but are not limited to: Nickel, Palladium, Gold, Gold-Palladium, Silver and Silver-Palladium, and other mixed-metal systems, and may include thin-film, plated, dip-coated, thick-film co-fired and/or post-fired metallized ceramic.

Bonding methods to connect discrete component terminations within a multilayer electrical interconnect structure include, without limitation: direct attach, thermal-reflow, wire-bond, laser-ribbon-bond, or alternate bonding process compatible with the interconnect metallizations and geometries. Typical capacitor geometries oftentimes require interconnect structures to be placed at opposite ends of the capacitor structure; however, an interconnect structure may be required at the top or bottom surfaces of the capacitor, depending on the architecture and electrical specifications of the devices.

Bonding materials for integration of a capacitor within a multilayer interconnect structure include, without limitation conductive composites (for example, a metal-filled thermosetting polymer system where the polymer may be an epoxy or polyimide-based and the metal may be Silver, Gold, other noble metal or mixtures thereof). Alternatively, solder, low-temperature braze or post-fire thick-film or co-fire thick-film can be used. An exemplary embodiment of the present invention utilizes compatible lead-interconnect materials and processes that reduce the equivalent-series-resistance (ESR) of the resulting integrated component or circuit. In the case of an integrated EMI capacitor, reduced ESR translates to reduced parasitic inductance and improved filtering performance.

In applications for IMDs where the design may require exposure of the integrated component and respective interconnections to corrosive bodily fluid (in an implantable sensor or sensor assembly for example), an interconnect metallization scheme that utilizes non-oxidizing metal layers such as noble metals may be used (e.g., Au, Pt, Pd and mixtures thereof). In applications where there may be a voltage-bias applied to the interconnect, an exemplary metal layer includes Platinum, or a less noble metallization system that is adequately passivated. Other metallizations that may be useful include niobium and titanium, or tantalum either used singly or in combination (layer form), or as an overlayer protection over less stable metals, such as Ni, Pd, Ag or combinations thereof. The inventors suggest that it may be desirable to provide a coating over the whole device as well as the interconnect regions, in which the coating material can include an organic polymer, such as a biocompatible siloxane-based polymer, or a dielectric oxide, such as a thin-film deposited Aluminum Oxide.

The following drawings depict several exemplary embodiments of the invention and are not intended as limiting but rather illustrative of certain aspects of the invention. The drawings are not drawn to scale and common reference numerals are used to denote similar elements of the invention.

DESCRIPTION OF THE ILLUSTRATED EMBODIMENTS

Figure 1:
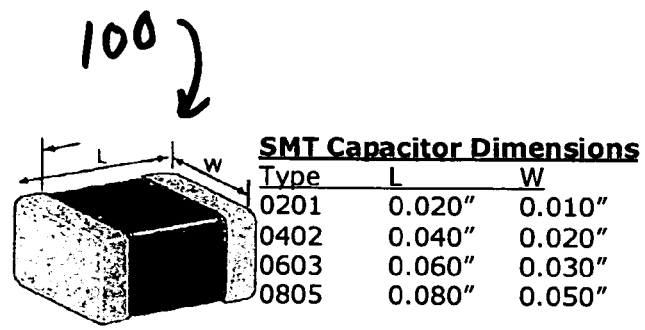
FIG. 1 depicts prior art surface mount technology (SMT) capacitor technologies for integration in co-fire technology wherein a surface-mount 'chip' capacitor can be integrated, although other types of capacitors can also be integrated (e.g., discoidal capacitors).

The following discussion is presented to enable a person skilled in the art to make and use the embodiments of the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives, which fall, within the scope of the invention.

Referring now to FIG. 1 which is a perspective view of a prior art surface mounted technology (SMT) capacitor 100 suitable for integration using LTCC or HTCC technology and a table including type codes and relative dimensions of such a capacitor 100.

It should be recognized that discoidal type and multi-interconnect (i.e,. multi-polar) type capacitors can also be integrated, as dictated by the performance and interconnect requirements of the device.

Figure 2:
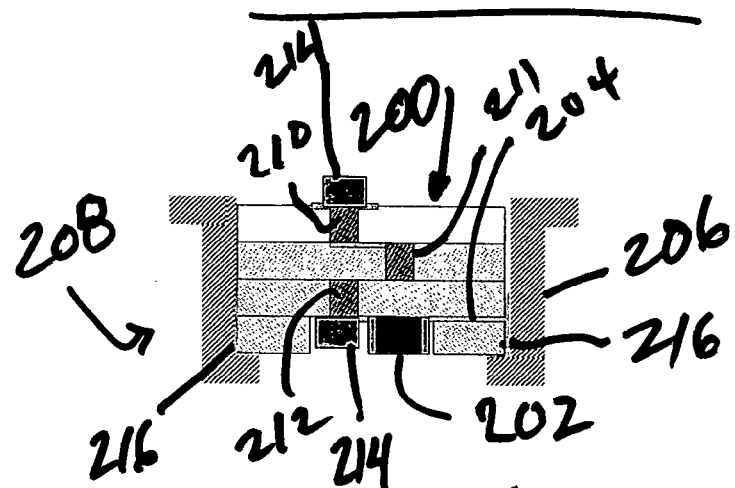
FIG. 2 depicts an elevational side view in cross section of a co-fired EMI capacitor disposed within a portion of a first, lower ceramic layer and wherein an embedded electrical layer grounds the EMI capacitor to the feedthrough ferrule.

Referring to FIG. 2 a co-fired, hermetic feedthrough structure 200 having a $1^{st}$-level cavity-buried EMI capacitor 202 with internal interconnect (conductive interlayer 204) coupled to an electrical ground reference (ferrule 206) is depicted schematically in an elevational cross section schematic view. Prior to physically coupling the hermetic feedthrough 200 to ferrule 206 to fabricate the integrated structure 208 the feedthrough is co-fired at elevated temperature. The resulting unipolar or mono-polar (single signal-conducting) feedthrough structure 208 thus includes a discrete passive electronic element mounted within and electrically coupled to the feedthrough structure 200. The electrically conducting via structures 210–212 provide a continuous electrical pathway from one or a pair of (optional) capture pads 214 that electrically couple to via structures 210 and/or 212. One pole of the passive element or elements 202 (e.g., capacitor, inductor, LC circuit, or the like) connects to at least one of the via structures 210–212 and/or a capture pad 214 that convey electrical signals through the structure 200. As depicted, a conductive trace between element (or elements) 202 couples to both via structure 212 and capture pad 214 although a single connection will suffice. The other pole of the element(s) 202 connects to ground or electrical reference potential (e.g., ferrule member 206) by one or more embedded interconnect or other conductive interlayer, conductive trace or other conductive element 204. In FIG. 2 the interlayer 204 electrically couples to a conductive braze 216 (e.g., gold) surrounding a lower portion of the structure 200 and conductively bonds the structure 200 to the ferrule 206. The resulting structure 208 is thus adapted for insertion into an aperture formed in a housing for an implantable medical device (not depicted in FIG. 2), such as a pacemaker, implantable pulse generator, drug pump, neurostimulator, a sensor capsule, and/or an electrochemical cell (e.g., battery, capacitor, etc.).

Figure 3:
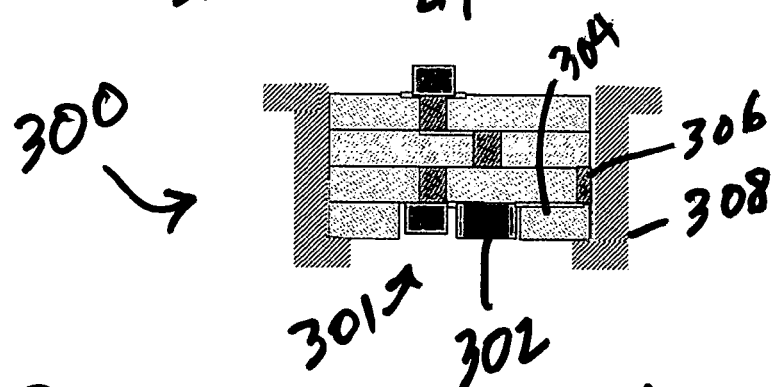
FIG. 3 depicts an elevational side view in cross section of a co-fired EMI capacitor disposed within a first, lower ceramic layer and wherein a side-castellation interconnect electrically couples to a reference, or ground, plane such as a feedthrough ferrule.

In FIG. 3, an integrated mono-polar structure 300 is depicted in an elevational cross-sectional view that is similar to the structure illustrated in FIG. 2. However, in FIG. 3, a $1^{st}$-level cavity-buried electrical element 302 (e.g., an EMI capacitor, inductor, LC circuit, or the like) and one pole of said element 302 (or elements) electrically couples to a side-castellation structure 306 which is turn is connected to an electrical reference or ground (ferrule 308) by conductive interlayer 304. The side-castellation structure 306 can comprise an additional independent via structure that is co-fired along with the rest of the components of feedthrough structure 301 and thus provides a robust, hermetic ground connection that is highly resistant to fluid ingress. The side-castellation structure 306 also optionally couples to a conductive braze material (e.g., gold) that bonds the ferrule 308 to the co-fired feedthrough 301.

Figure 4:
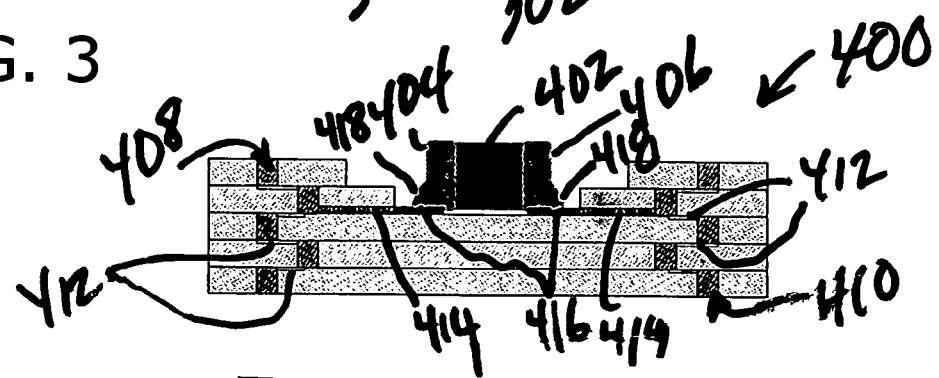
FIG. 4 depicts an elevational side view in cross section of a co-fired EMI capacitor disposed within a multi-polar, co-fired feedthrough

Turning now to FIG. 4, which is an elevational view in cross-section of a multipolar co-fired feedthrough structure 400 having a discrete passive electronic device or circuit 402 mounted within the structure 400. Each pole 404, 406 of the device or circuit 402 couples to a one of two independent serpentine conductive via structures that each provide an electrical pathway 408, 410 to both sides of the structure 400. While the electrical pathways 408, 410 are depicted as fabricated with offset via structures coupled together with discrete similarly offset serpentine interlayers 412, one or both of the pathways 408, 410 can be fabricated with substantially axially-aligned via structures. A pair of robust conductive interlayers 414 extends from at least one of the via structures or interlayers 412 toward one pole 404, 406 of the element or circuit 402. The element or circuit 402 couples to a pair of capture pads 416 that independently electrically couple to the interlayers 414 and/or 412. The element or circuit 402 can optionally be bonded to one or both of the capture pads 416 using, for example a braze material 418 (e.g., gold).

Figure 5:
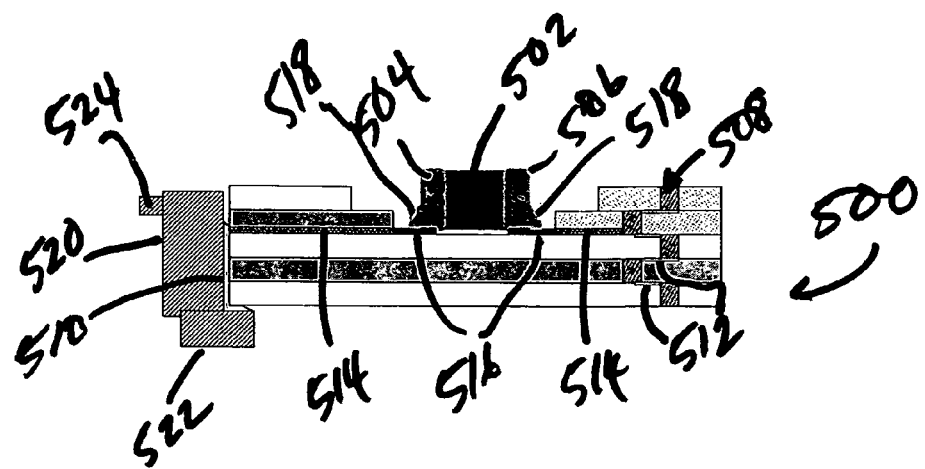
FIG. 5 depicts an elevational side view in cross section of a co-fired EMI capacitor having a second level, embedded, or cavity-buried, EMI capacitor with a signal communicated through a reference, or electrical ground, to a portion of a metallic ferrule surrounding the feedthrough.

FIG. 5 depicts a co-fired electrical feedthrough 500 coupled to a ferrule 520 and a support structure 522. Said feedthrough 500 supports and electrically couples to a $2^{nd}$-level cavity-buried electrical element or circuit 502 (as depicted an EMI capacitor for filtering signals conducted through the feedthrough 500). One pole 504 of the element or circuit 502 electrically couples to an electrical reference or ground (in FIG. 5 ferrule 520). The discrete capacitor 502 is depicted as being mounted deeper within a recessed area or cavity of the feedthrough 500. The element or circuit 502 can of course be mounted deeper within the recessed area or can be mounted above or below the height of the upper surface of the multilayer feedthrough structure 500. Although as drawn FIG. 5 is an elevational view in cross-section of a multipolar co-fired feedthrough structure 500 having a discrete passive electronic device or circuit 502 mounted within the structure 500, the structure 500 can have any arbitrary shape or configuration (i.e., if depicted in a plan view). Likewise, the recessed area where the element or circuit 502 resides can also have any arbitrary shape, including circular, rectangular, irregular, and the like. A second pole 506 of the device or circuit 502 couples to an independent serpentine conductive via structure (depicted by arrow 508) that provides an electrical pathway to opposing sides of the structure 500. While the electrical pathway 508 is depicted as fabricated with offset via structures coupled together with discrete similarly offset serpentine interlayers 512, the pathway 508 can be fabricated with substantially axially-aligned via structures. A pair of robust conductive interlayers 514 extends from the via structure or interlayer 512 toward the pole 506 of the element or circuit 502. The element or circuit 502 couples to a pair of capture pads 516 that independently electrically couple to the interlayers 514 and/or 512. The element or circuit 502 can optionally be bonded to one or both of the capture pads 516 using, for example a conductive braze material 518 (e.g., gold). In FIG. 5 the braze material 518 hermetically bonds to both the ferrule 520 and a lower mechanical support member 522. Also bonded to the ferrule 520 is an edge portion of an aperture of a medical device or electrochemical cell 524. The reader should note that only one side of ferrule 520, support member 522 and the periphery of the aperture of the medical device or electrochemical cell 524 is illustrated.

Figure 6:
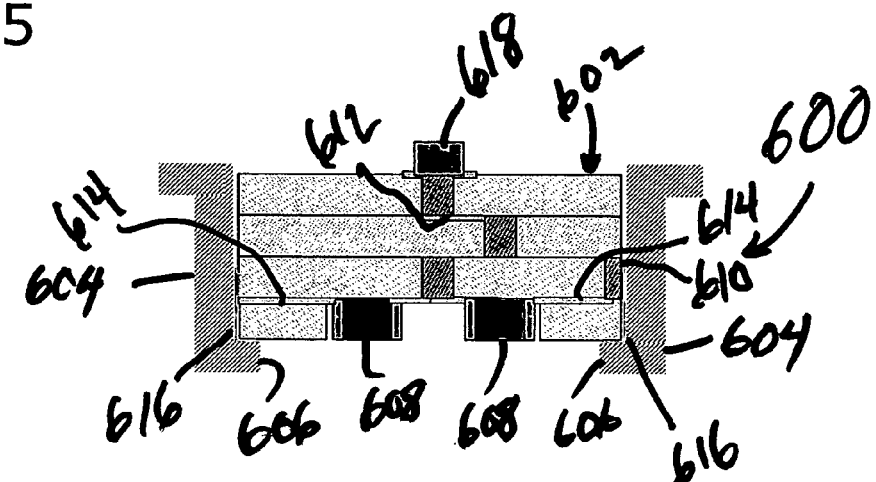
FIG. 6 depicts an elevational side view in cross section of a co-fired EMI capacitor having a pair of embedded, or cavity-buried, EMI capacitors electrically coupled thereto.

Turning now to FIG. 6, wherein an integrated assembly 600 comprising a co-fired multilayer feedthrough structure 602 hermetically couples to a ferrule member 604. In lieu of the ferrule (520) and support member (522) depicted in FIG. 5, the ferrule member 604 comprises a unitary member including a lower support shelf for supporting and bonding to feedthrough 602. In FIG. 6 a pair of cavity-buried electrical components or circuits 608 couple to an interior or lower portion of the integrated assembly 600 (as depicted, EMI capacitors). Of course, as earlier noted, more than one discrete component or circuit 608 can be physically integrated into and electrically coupled to an electrical pathway of the feedthrough structure 602 (e.g., electrically coupled serpentine via structures with conductive interlayers 614 therebetween). For example, the electromagnetic filtering requirements of a given implantable medical device may require the use of two or more components or circuits 608 integrated within the integrated assembly 600. One pole of each of the components or circuits 608 couples to the conductive serpentine via structure. The other pole of a first one of the components 608 couples to an electrical reference or ground (ferrule 604 and/or conductive braze 616) by interlayer 614. The other pole of a second of the components 608 couples to an electrical reference or ground side-castellation 610 (and/or ferrule 604 and/or conductive braze 616). An optional capture pad 618 couples to an upper, surface-level via structure of the feedthrough structure 602. The fully fabricated (e.g., co-fired and brazed) assembly 600 is then adapted for insertion into an aperture of a medical device or electrochemical cell (not shown in FIG. 6).

Figure 7:
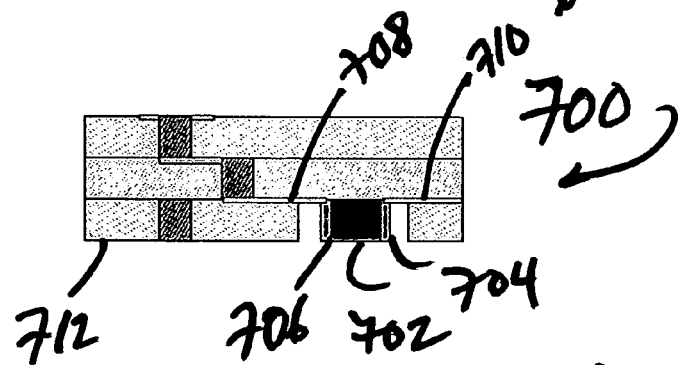
FIG. 7 depicts an elevational side view in cross section of a co-fired EMI capacitor having an isolated, interconnected integrated capacitor spaced from an adjacent metallized (i.e., electrical signal bearing) via.

FIG. 7 is an elevational view in cross-section of a co-fired feedthrough 700 having an isolated, interconnected passive electrical component or circuit 702. The component or circuit 702 is physically coupled to the feedthrough 700 in a recessed area (e.g., an aperture or bore of an outer layer 712 of the feedthrough 700). Part of what is illustrated in FIG. 7 is a component or circuit 702 spaced apart away from the electrical signal pathway feedthrough but electrically coupled by one or more embedded interlayers 708, 710. Such an arrangement can be used to isolate, for example, a capacitor that might be susceptible to so-called fringe effects of electrical signals.

Figure 8:
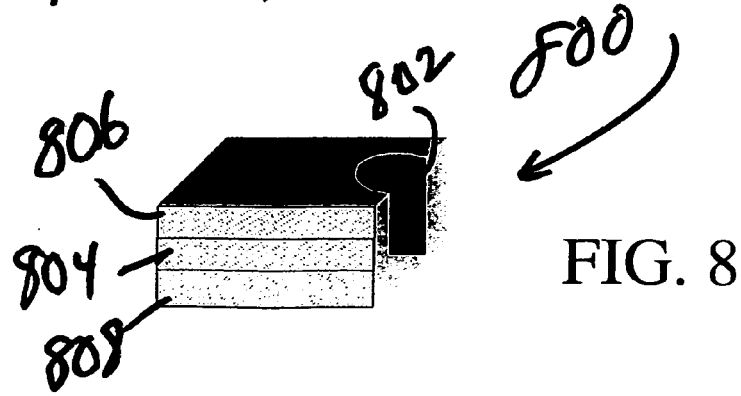
FIG. 8 depicts a perspective view of a co-fired EMI capacitor having a side castellation via/interconnect.

In FIG. 8 one embodiment of a side-castellation type via structure 802 is illustrated in a perspective view in partial cross-section. Such a via structure 802 can be disposed on a peripheral portion of an interior layer 804, 808 and/or can be fabricated so that it is exposed to an outer surface of a layer 806.

Figure 9:
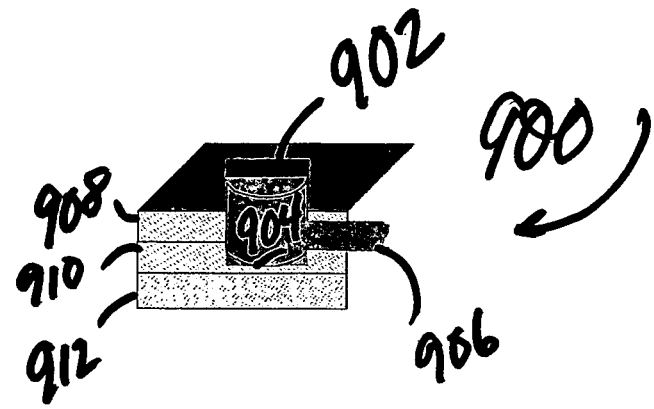
FIGS. 9 and 10 depict a perspective view of a co-fired EMI capacitor having a via-interconnect electrically coupled to a cavity to enable electrical communication with an integrated electrical component residing adjacent and/or on a portion of the interconnect.

FIG. 9 is a perspective view with certain interior components of a hermetic co-fired feedthrough 900 fabricated of multiple layers 908, 910, 912. A surface interconnect member or capture pad 902 couples to layer 908 and to a conductive via structure 904 (as depicted a cylinder-shaped member extending through two layers 908, 910). An interior interlayer 906 couples to the via structure 904 at one end of the interlayer 906 and to a remote component, via structure, electrical ground, or the like (not shown). The type of structure depicted in FIG. 9 lends itself to surface mounting of conductors, components, circuits and the like to the surface interconnect member or capture pad 902.

Figure 10:
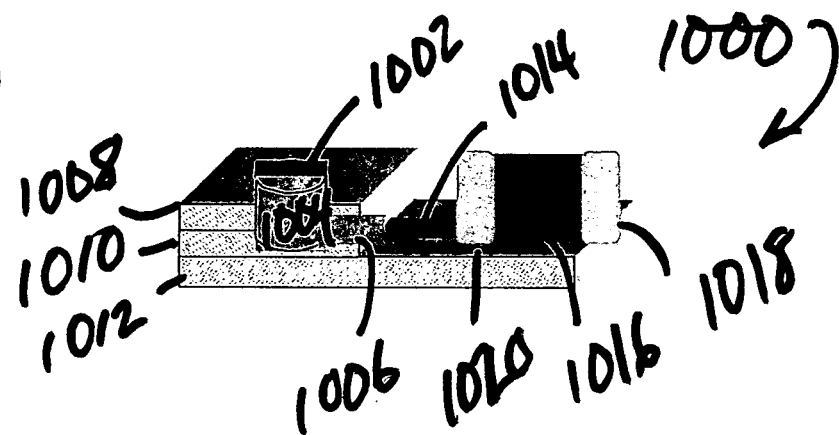

FIG. 10 is a perspective view with certain interior components of a hermetic co-fired feedthrough assembly 1000 including a recess-mounted component 1016 (e.g., a circuit, a conductor or the like) fabricated of multiple layers 1008, 1010, 1012. A surface interconnect member or capture pad 1002 couples to layer 1008 and to a conductive via structure 1004 (as depicted a cylinder-shaped member extending through two layers 1008, 1010). Of course, as with FIG. 9 the via structure 1004 depicted in FIG. 10 can occupy an aperture formed in a single layer (e.g., 1008). An interior interlayer 1006 couples to the via structure 1004 at one end of the interlayer 1006 and to a first pole 1020 of a remote component 1016 (e.g., a via structure, an electrical ground, a conductor, or the like). The type of structure depicted in FIG. 10 lends itself to surface mounting or attachment of conductors, components, circuits and the like to the surface interconnect member or capture pad 1002 while also reducing the overall volume of the assembly 1000 in part by use of suitably recessed area for component(s) 1016.

Figure 11:
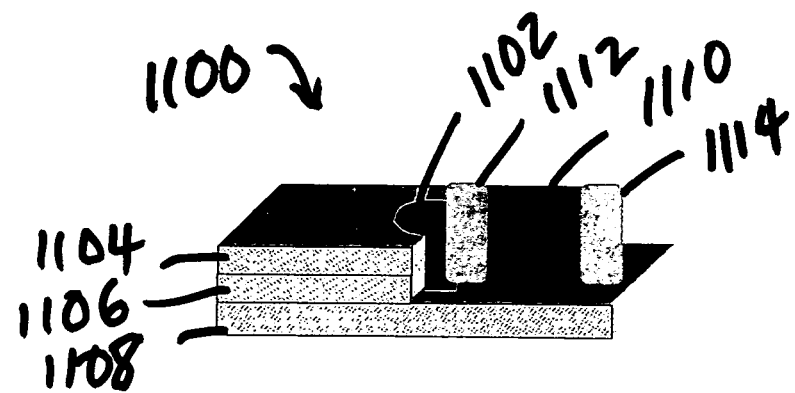
FIG. 11 depicts a perspective view of a co-fired EMI capacitor having a side-castellation electrically coupled a cavity-mounted SMT EMI capacitor.

FIG. 11 is a perspective view with certain interior components of a hermetic co-fired feedthrough assembly 1100 including a recess-mounted component, circuit, conductor or the like fabricated of multiple layers 1104, 1106, 1108 and having a side-castellation 1102 formed within a pair of the layers 1104, 1106. As illustrated the side-castellation 1102 extends to the upper surface of the layer 1104. At least a portion of side-castellation 1102 directly couples to a first pole 1112 or a component or circuit 1110. The other pole of the component or circuit 1110 is thus accessible for additional electrical couplings or the like.

In some embodiments of the invention, the feedthrough functionally couples to the periphery of a receiving aperture or port using brazing techniques. As is known in the art, brazing involves joining two discrete parts by fusing a layer of a brazing material (e.g. a metal such as gold) between adjoining surfaces of the parts. Generally, the process involves a braze melting and flowing between the two parts, commonly referred to as wetting. The braze material may form an interlayer that provides a suitable thermochemical and hermetic seals between the joined parts. In some embodiments, the parts are coupled using reactive metal brazing (RMB) techniques. Such RMB techniques utilize individual RMB foils (or preformed pieces) or the RMB may be formed directly between the parts to be joined using suitable thin-film deposition processes. In other embodiments the parts functionally couple by other techniques such as, for example, diffusion bonding techniques. Generally speaking, diffusion bonding involves holding components under load at elevated temperature in a protective atmosphere or vacuum. The loads used are typically lower than those that cause macrodeformation of the components. Bonding operations may be performed under vacuum or in an inert gas atmosphere, or, in some embodiments, in air. Diffusion bonding may also include the use of interlayers and the formation of a transient liquid phase thereof. Further, in some embodiments a eutectic joint can be formed. This is similar to other joining methods that include intimate contact and application of elevation temperature except the two materials that form the eutectic joint possess a lower melting point than either adjacent substrate. Further, a localized eutectic joint can be formed via applied laser energy since the temperature of the pieces themselves are not elevated to form the bond. In such embodiments the stresses (e.g. due to TCE mismatch) at service temperature are less. The localized heat may also be provided by patterned resistors on the substrate or by inductively coupled metal traces.

The green-sheet is typically a polymer-ceramic composite that is comprised of an organic (polymer) binder filled with glass, ceramic, or glass-ceramic or mixtures thereof. The organic binder may also contain plasticisers and dispersants. To form electrically conductive pathways, thick-film metal inks and pastes are used to form pre-cursor pathways that form electrically conducting pathways following co-firing. Thick-film pastes or inks may contain metal for formation of electrical pathways or dielectrics for formation of integrated passives such as resistors and capacitors. The organic vehicle may contain polymers, solvents and plasticisers. Thick-film technology is further described in J. D. Provance, "Performance Review of Thick Film Materials", Insulation/Circuits, (April 1977), and in Morton L. Topfer, "Thick-film Microelectronics, Fabrication, Design, and Applications (1977), pp. 41–59, the contents of each of which are hereby incorporated by reference.

Thus, embodiments of the IMPLANTABLE CO-FIRED ELECTRICAL INTERCONNECT SYSTEMS AND DEVICES AND METHODS OF FABRICATION THEREFOR are disclosed. One skilled in the art will appreciate that the invention can be practiced with embodiments other than those disclosed. The disclosed embodiments are presented for purposes of illustration and not limitation, and the invention is limited only by the claims that follow.

We claim:

1. A hermetic electrical interconnect for an implantable medical device (IMD), comprising:
    a monolithic structure derived from at least three discrete ceramic green-sheet layers having at least one continuous electrical pathway disposed through at least one bore coupling opposing major surfaces of each of the at least three layers; and
    a first pole of a first passive electrical component coupled to the at least one continuous electrical pathway, wherein said at least one electrical component physically couples to a recessed region of the monolithic structure,
    wherein said monolithic structure and the first passive electrical component are hermetically coupled to an IMD.

2. A hermetic electrical interconnect according to claim 1, wherein the continuous electrical pathway comprises a plurality of offset individual metal-filled via structures and further comprising at least one conductive interlayer electrically coupling a pair of the individual metal-filled via structures.

3. A hermetic electrical interconnect according to claim 1, wherein the IMD comprises one of: an electrochemical cell, a pacemaker, a implantable cardioverter-defibrillator, a drug pump, a neurological stimulator, an implantable pulse generator, a sensor capsule.

4. A hermetic electrical interconnect according to claim 1, wherein the electrical component comprises at least one of: a capacitor, a resistor, an inductor, a self-resonant inductor-capacitor circuit.

5. A hermetic electrical interconnect according to claim 1, further comprising at least a second passive electrical component coupled to one of the first passive electrical component and the at least one continuous electrical pathway.

6. A hermetic electrical interconnect according to claim 1, further comprising a ferrule member sealingly surrounding a peripheral portion said monolithic structure.

7. A hermetic electrical interconnect according to claim 6, further comprising an aperture formed through a portion of one of an enclosure of an IMD and an electrochemical cell, said aperture configured to sealingly receive peripheral edges of the ferrule member.

8. A hermetic electrical interconnect according to claim 7, further comprising an electrically conductive braze material physically coupling the monolithic structure to said ferrule member.

9. A hermetic electrical interconnect according to claim 6, wherein said ferrule member includes one of a lower support shelf and a discrete lower support member adapted to mechanically support a portion of said monolithic structure.

10. A hermetic electrical interconnect according to claim 1, wherein the at least one continuous electrical pathway comprises a second electrical pathway and said second electrical pathway couples to a second pole of said first passive electrical component.

11. A hermetic electrical interconnect according to claim 1, wherein a second pole of said first passive electrical component electrically couples to an electrical reference.

12. A hermetic electrical interconnect according to claim 11, wherein the electrical reference comprises a conductive pathway extending to the ferrule member.

13. A hermetic electrical interconnect according to claim 12, further comprising a side-castellation structure coupled to the ferrule member and the conductive pathway.

14. A hermetic electrical interconnect according to claim 13, wherein said side-castellation structure comprises a sintered member co-fired when the monolithic structure and continuous conductive pathway were co-fired.

15. A hermetic electrical interconnect according to claim 1, further comprising at least one conductive bonding pad coupled to an opposing major surfaces and operatively coupled to the at least one continuous electrical pathway.

16. A hermetic electrical interconnect structure adapted for use in an implantable medical device (IMD), comprising:
    a multi-layer integrated and co-fired structure, said co-fired structure further including:
        at least three layers of a ceramic material with each of said at least three layers having an aperture formed therethrough and wherein the ceramic material possesses a characteristic coefficient of thermal expansion;
        a volume of a conductive metallic sintered-paste at least partially filling the aperture of said at least three layers, said metallic sintered-paste having a characteristic coefficient of thermal expansion approximately the same as the characteristic coefficient of thermal expansion of said ceramic material;
        a metallic interlayer disposed in contact with the aperture of said at least three layers, said metallic interlayer also having a characteristic coefficient of thermal expansion approximately the same as the characteristic coefficient of thermal expansion of said ceramic material; and
        a first pole of a first passive electrical component coupled to at least one of the metallic sintered-paste and the metallic interlayer, wherein said first passive electrical component physically couples to a recessed region formed a portion of one of the at least three layers of ceramic material; and
    a ferrule member hermetically coupled to a lateral periphery of said multi-layer integrated and co-fired structure, wherein said ferrule member is adapted for hermetic insertion into an aperture formed in one of a housing for an IMD.

17. A hermetic electrical interconnect structure according to claim 16, further comprising a weld flange disposed around an outer periphery of said ferrule member.

18. A hermetic electrical interconnect structure according to claim 16, further comprising a high-temperature braze joint hermetically sealingly the ferrule member to the multi-layer integrated and co-fired structure.

19. A hermetic electrical interconnect structure according to claim 17, wherein the ferrule member includes one of a lower support shelf feature and a second member, said shelf feature and said second member adapted to support a part of the multi-layer integrated and co-fired structure and further comprising a hermetic diffusion bond disposed between a portion of the multi-layer integrated and co-fired structure and the ferrule member.

20. A hermetic electrical interconnect structure according to claim 17, wherein the IMD comprises one of: an electrochemical cell, a pacemaker, a implantable cardioverter-defibrillator, a drug pump, a neurological stimulator, an implantable pulse generator, a capsule enclosing an implantable physiologic sensor.

* * * * *